United States Patent [19]
Luther et al.

[11] Patent Number: 5,913,848
[45] Date of Patent: Jun. 22, 1999

[54] HARD TIP OVER-THE-NEEDLE CATHETER AND METHOD OF MANUFACTURING THE SAME

[75] Inventors: Ronald B. Luther, Newport Beach; Charles W. Dickerson, Tustin; Richard A. Overton, Anaheim, all of Calif.; Harold Pearsall, Sandy, Utah

[73] Assignee: Luther Medical Products, Inc., Tustin, Calif.

[21] Appl. No.: 08/659,450

[22] Filed: Jun. 6, 1996

[51] Int. Cl.$^6$ .......................... A61M 25/00; A61M 5/178
[52] U.S. Cl. ........................ 604/282; 604/164; 604/280
[58] Field of Search .................................. 604/280, 281, 604/282

[56] References Cited

U.S. PATENT DOCUMENTS

| | | |
|---|---|---|
| 268,632 | 12/1882 | Danforth . |
| 561,059 | 5/1896 | Mitchell et al. . |
| 995,288 | 6/1911 | Place . |
| 1,248,492 | 12/1917 | Hill . |
| 2,001,638 | 5/1935 | Tornsjo ................................... 128/347 |
| 2,571,653 | 10/1951 | Bastien .................................... 128/218 |
| 2,623,520 | 12/1952 | Bamford, Jr. et al .................. 128/221 |
| 2,623,521 | 12/1952 | Shaw ....................................... 128/221 |
| 2,847,995 | 8/1958 | Adams ..................................... 128/214 |
| 2,876,770 | 3/1959 | White ....................................... 128/215 |
| 2,925,083 | 2/1960 | Craig ........................................ 128/218 |
| 3,030,953 | 4/1962 | Koehn ..................................... 128/214 |
| 3,063,451 | 1/1962 | Kowalk .................................... 128/221 |
| 3,137,299 | 6/1964 | Tabor ....................................... 128/351 |
| 3,225,762 | 12/1965 | Guttman .................................. 128/214 |

(List continued on next page.)

FOREIGN PATENT DOCUMENTS

| | | |
|---|---|---|
| 813433 | 7/1949 | Germany . |
| 2121699 | 7/1980 | Germany . |
| 0924734 | 5/1963 | United Kingdom . |
| 1131865 | 10/1968 | United Kingdom . |
| 1233302 | 5/1971 | United Kingdom . |
| 1297746 | 11/1972 | United Kingdom . |
| 0008451 | 3/1980 | United Kingdom . |
| 0023580 | 2/1981 | United Kingdom . |
| 2059268 | 4/1981 | United Kingdom . |
| 2114006 | 8/1983 | United Kingdom . |
| 0039872 | 5/1985 | United Kingdom . |

(List continued on next page.)

OTHER PUBLICATIONS

Menlo Care, Inc., "Landmark Venous Access Device" —2 pages.
ICU Medical, Inc., The First of Defense Against Needle Stick Injuries, Introducing the ICU HR Needle, 4 pages.
Baxter HealthCare Corporation, "Intrasil and Centrasil Catheters Line Up the Best Features for Central Venous IV", 7 pages.
Vygon Corporation, "Lifevac PICC Lines", 5 pages.
The Gesco Per–Q–Cath, "A Percutaneously Inserted Catheter with the Excalibur Introducer", 4 pages.
Luther Medical Products, Inc., "L–Cath Peel–Away", 4 pages.

*Primary Examiner*—Sam Rimell
*Assistant Examiner*—Robert V. Racunas
*Attorney, Agent, or Firm*—Setina Brunda Garred & Brucker

[57] ABSTRACT

An over-the-needle catheter for insertion into an anatomical passage through the use of an introducer. The catheter comprises an elongate, flexible catheter body defining proximal and distal ends, and a lumen extending longitudinally therethrough. Partially inserted into and protruding from the distal end of the catheter body is a rigid, tubular sleeve which defines an abutment shoulder within the lumen of the catheter body. Disposed on and encapsulating the exposed portion of the sleeve is a distal tip member defining a central opening which communicates with the lumen via the sleeve. The abutment shoulder is adapted to abut a portion of the introducer in a manner which inhibits proximal movement of the tip member relative to the introducer to prevent the tip member from being pushed proximally over the introducer and collapsing the catheter body during the insertion of the catheter into the anatomical passage.

13 Claims, 2 Drawing Sheets

U.S. PATENT DOCUMENTS

| | | | |
|---|---|---|---|
| 3,312,220 | 4/1967 | Eisenberg | 128/214.4 |
| 3,323,523 | 6/1967 | Scislowicz et al. | 128/214.4 |
| 3,344,786 | 10/1967 | Berg et al. | 128/215 |
| 3,348,544 | 10/1967 | Braun | 128/214.4 |
| 3,352,306 | 11/1967 | Hirsch | 128/214.4 |
| 3,406,685 | 10/1968 | May | 128/214.4 |
| 3,454,006 | 7/1969 | Langdon | 128/214.4 |
| 3,459,183 | 8/1969 | Ring et al. | 128/21.4 |
| 3,463,152 | 8/1969 | Sorenson | 128/214.4 |
| 3,491,756 | 1/1970 | Bentov | 128/221 |
| 3,536,073 | 10/1970 | Farb | 128/214.4 |
| 3,539,034 | 11/1970 | Tafeen | 128/221 |
| 3,540,447 | 11/1970 | Howe | 128/221 |
| 3,547,119 | 12/1970 | Hall et al. | 128/214.4 |
| 3,566,874 | 3/1971 | Shepherd et al. | 128/349 |
| 3,574,306 | 4/1971 | Alden | 128/214.4 |
| 3,595,230 | 7/1971 | Suyeoka et al. | 128/214.4 |
| 3,598,118 | 8/1971 | Warren | 128/214.4 |
| 3,598,127 | 8/1971 | Wepsic | 128/349 |
| 3,610,240 | 10/1971 | Harautuneian | 128/214.4 |
| 3,612,050 | 10/1971 | Sheridan | 128/214.4 |
| 3,625,741 | 12/1971 | Stoy et al. | 117/75 |
| 3,630,195 | 12/1971 | Santomieri | 128/133 |
| 3,630,198 | 12/1971 | Henkin | 128/215 |
| 3,658,061 | 4/1972 | Hall | 128/214.4 |
| 3,693,624 | 9/1972 | Shilley et al. | 128/351 |
| 3,720,210 | 3/1973 | Diettrich | 128/214.4 |
| 3,788,318 | 1/1974 | Kim et al. | 128/214.4 |
| 3,792,703 | 2/1974 | Moorehead | 128/214.4 |
| 3,809,081 | 5/1974 | Loveless | 128/214.4 |
| 3,811,449 | 5/1974 | Gravelee et al. | 128/214.4 |
| 3,833,003 | 9/1974 | Taricco | 128/347 |
| 3,834,380 | 9/1974 | Boyd | 128/133 |
| 3,844,296 | 10/1974 | Armstrong | 131/186 |
| 3,875,938 | 4/1975 | Mellor | 128/214.4 |
| 3,884,230 | 5/1975 | Wulff | 128/221 |
| 3,890,971 | 6/1975 | Leeson et al. | 128/218 R |
| 3,904,033 | 9/1975 | Haerr | 206/349 |
| 3,915,168 | 10/1975 | Monestere, Jr. et al. | 128/214.4 |
| 3,923,066 | 12/1975 | Francisoud et al. | 128/348 |
| 3,946,741 | 3/1976 | Adair | 128/347 |
| 3,961,862 | 6/1976 | Edstrom et al. | 417/282 |
| 3,995,623 | 12/1976 | Blake et al. | 128/2.06 E |
| 4,013,080 | 3/1977 | Froning | 128/347 |
| 4,020,835 | 5/1977 | Nordstrom et al. | 128/214.4 |
| 4,029,105 | 6/1977 | Faust | 128/351 |
| 4,040,428 | 8/1977 | Clifford | 128/351 |
| 4,072,146 | 2/1978 | Howes | 128/2.05 D |
| 4,073,297 | 2/1978 | Kopp | 128/214.4 |
| 4,108,175 | 8/1978 | Orton | 128/214.4 |
| 4,160,450 | 7/1979 | Doherty | 128/214.4 |
| 4,170,993 | 10/1979 | Alvarez | 128/214 R |
| 4,177,814 | 12/1979 | Knepshield et al. | 128/348 |
| 4,183,884 | 1/1980 | Wichterie et al. | 264/41 |
| 4,194,504 | 3/1980 | Harms et al. | 128/214.4 |
| 4,377,165 | 3/1983 | Luther et al. | 128/214.4 |
| 4,392,856 | 7/1983 | Lichtenstein | 604/177 |
| 4,406,656 | 9/1983 | Hattler et al. | 604/280 |
| 4,416,273 | 11/1983 | Grimes | 128/207.16 |
| 4,417,886 | 1/1991 | Frankhouser et al. | 604/53 |
| Re. 4,417,886 | 11/1983 | Frankhouser et al. | 604/53 |
| 4,425,120 | 1/1984 | Sampson et al. | 604/198 |
| 4,431,426 | 2/1984 | Groshong et al. | 604/280 |
| 4,434,797 | 3/1984 | Silander | 128/343 |
| 4,434,810 | 3/1984 | Atkinson | 137/493 |
| 4,439,583 | 3/1984 | Gould et al. | 525/127 |
| 4,449,973 | 5/1984 | Luther | 604/161 |
| 4,468,224 | 8/1984 | Enzmann et al. | 604/247 |
| 4,480,642 | 11/1984 | Stoy et al. | 128/341 |
| 4,500,312 | 2/1985 | McFarlane | 604/263 |
| 4,501,933 | 2/1985 | Siligoni et al. | 179/81 R |
| 4,506,665 | 3/1985 | Andrews et al. | 128/202.27 |
| 4,509,945 | 4/1985 | Kramann et al. | 604/164 |
| 4,512,346 | 4/1985 | Lemole | 128/335 |
| 4,515,583 | 5/1985 | Sorich | 604/22 |
| 4,525,157 | 6/1985 | Vaillancourt | 604/52 |
| 4,529,399 | 7/1985 | Groshong et al. | 604/53 |
| 4,535,773 | 8/1985 | Yoon | 604/51 |
| 4,540,411 | 9/1985 | Bodicky | 604/169 |
| 4,549,879 | 10/1985 | Groshong et al. | 604/27 |
| 4,559,046 | 12/1985 | Groshong et al. | 604/282 |
| 4,569,675 | 2/1986 | Prosl et al. | 604/175 |
| 4,573,976 | 3/1986 | Sampson et al. | 604/198 |
| 4,573,981 | 3/1986 | McFarlane | 604/263 |
| 4,580,573 | 4/1986 | Quinn | 128/657 |
| 4,588,398 | 5/1986 | Daugherty | 604/265 |
| 4,596,593 | 6/1986 | Pande | 604/264 |
| 4,610,671 | 9/1986 | Luther | 604/168 |
| 4,613,329 | 9/1986 | Bodicky | 604/158 |
| 4,627,841 | 12/1986 | Dorr | 604/158 |
| 4,631,057 | 12/1986 | Mitchell | 604/198 |
| 4,636,199 | 1/1987 | Victor | 604/164 |
| 4,643,199 | 2/1987 | Jennings, Jr. et al. | 128/763 |
| 4,652,256 | 3/1987 | Vaillancourt | 604/52 |
| 4,655,751 | 4/1987 | Harbaugh | 604/198 |
| 4,664,259 | 5/1987 | Landis | 206/365 |
| 4,664,653 | 5/1987 | Sagstetter et al. | 604/197 |
| 4,664,654 | 5/1987 | Strauss | 604/198 |
| 4,666,435 | 5/1987 | Braginetz | 604/198 |
| 4,668,221 | 5/1987 | Luther | 604/164 |
| 4,668,225 | 5/1987 | Russo et al. | 604/270 |
| 4,671,795 | 6/1987 | Mulchin | 604/281 |
| 4,671,796 | 6/1987 | Groshong et al. | 604/247 |
| 4,673,394 | 6/1987 | Fenton, Jr. et al. | 604/175 |
| 4,674,498 | 6/1987 | Stasz | 128/303.14 |
| 4,676,783 | 6/1987 | Jagger et al. | 604/171 |
| 4,680,029 | 7/1987 | Ranford et al. | 604/280 |
| 4,690,675 | 9/1987 | Katz | 604/177 |
| 4,695,274 | 9/1987 | Fox | 604/198 |
| 4,701,166 | 10/1987 | Groshong et al. | 604/247 |
| 4,702,735 | 10/1987 | Luther et al. | 604/161 |
| 4,702,738 | 10/1987 | Spencer | 604/198 |
| 4,702,739 | 10/1987 | Milorad | 604/198 |
| 4,721,506 | 1/1988 | Teves | 604/51 |
| 4,725,267 | 2/1988 | Vaillancourt | 604/192 |
| 4,728,322 | 3/1988 | Walker et al. | 604/165 |
| 4,731,068 | 3/1988 | Hesse | 604/110 |
| 4,739,768 | 4/1988 | Engelson | 128/658 |
| 4,747,831 | 5/1988 | Kulli | 604/110 |
| 4,753,640 | 6/1988 | Nichols et al. | 604/247 |
| 4,759,356 | 7/1988 | Muir | 128/207.16 |
| 4,762,516 | 8/1988 | Luther | 604/164 |
| 4,769,016 | 9/1988 | Labianca | 604/280 |
| 4,770,655 | 9/1988 | Haber et al. | 604/110 |
| 4,772,264 | 9/1988 | Cragg | 604/158 |
| 4,772,266 | 9/1988 | Groshong | 604/164 |
| 4,772,276 | 9/1988 | Wiita et al. | 604/283 |
| 4,773,901 | 9/1988 | Norton | 604/265 |
| 4,778,453 | 10/1988 | Lopez | 604/110 |
| 4,781,692 | 11/1988 | Jagger, et al. | 604/164 |
| 4,781,703 | 11/1988 | Walker et al. | 604/264 |
| 4,790,817 | 12/1988 | Luther | 604/53 |
| 4,790,828 | 12/1988 | Dombrowski et al. | 604/198 |
| 4,798,597 | 1/1989 | Vaillancourt | 604/270 |
| 4,800,890 | 1/1989 | Cramer | 128/657 |
| 4,801,297 | 1/1989 | Mueller | 604/280 |
| 4,826,490 | 5/1989 | Byrne et al. | 604/198 |
| 4,828,547 | 5/1989 | Sahi et al. | 604/110 |
| 4,828,549 | 5/1989 | Kvalo | 604/164 |
| 4,832,693 | 5/1989 | Gloyer | 604/110 |
| 4,832,696 | 5/1989 | Luther et al. | 604/164 |
| 4,834,708 | 5/1989 | Pullari | 604/165 |

| | | | |
|---|---|---|---|
| 4,834,718 | 5/1989 | McDonald | 604/195 |
| 4,838,881 | 6/1989 | Bennett | 604/280 |
| 4,840,622 | 6/1989 | Hardy | 604/264 |
| 4,846,186 | 7/1989 | Box et al. | 128/657 |
| 4,846,799 | 7/1989 | Tanaka et al. | 604/158 |
| 4,846,805 | 7/1989 | Sitar | 604/165 |
| 4,846,809 | 7/1989 | Sims | 604/198 |
| 4,846,811 | 7/1989 | Vanderhoff | 604/263 |
| 4,846,812 | 7/1989 | Walker | 604/264 |
| 4,850,961 | 7/1989 | Wanderer et al. | 604/53 |
| 4,863,431 | 9/1989 | Vaillancourt | 604/168 |
| 4,863,432 | 9/1989 | Kvalo | 604/177 |
| 4,869,717 | 9/1989 | Adair | 604/51 |
| 4,880,410 | 11/1989 | Rossmark | 604/110 |
| 4,883,699 | 11/1989 | Aniuk et al. | 428/36.9 |
| 4,887,998 | 12/1989 | Martin et al. | 604/110 |
| 4,895,564 | 1/1990 | Farrell | 604/164 |
| 4,896,680 | 1/1990 | Hirshowitz | 606/218 |
| 4,898,591 | 2/1990 | Jang et al. | 604/282 |
| 4,911,691 | 3/1990 | Aniuk et al. | 604/164 |
| 4,917,671 | 4/1990 | Chang | 604/168 |
| 4,927,415 | 5/1990 | Brodsky | 604/164 |
| 4,931,047 | 6/1990 | Broadwin et al. | 604/22 |
| 4,944,725 | 7/1990 | McDonald | 604/164 |
| 4,944,728 | 7/1990 | Carrell et al. | 604/164 |
| 4,950,252 | 8/1990 | Luther et al. | 604/198 |
| 4,955,863 | 9/1990 | Walker et al. | 604/165 |
| 4,957,488 | 9/1990 | Cameron et al. | 604/161 |
| 4,957,489 | 9/1990 | Cameron et al. | 604/161 |
| 4,964,854 | 10/1990 | Luther | 604/166 |
| 4,973,319 | 11/1990 | Melsky | 604/247 |
| 4,976,704 | 12/1990 | McLees | 604/265 |
| 4,986,814 | 1/1991 | Burney et al. | 604/164 |
| 4,994,046 | 2/1991 | Wesson et al. | 604/198 |
| 4,994,047 | 2/1991 | Walker et al. | 604/264 |
| 4,995,863 | 2/1991 | Nichols et al. | 604/247 |
| 4,998,919 | 3/1991 | Schnepp-Pesch et al. | 604/164 |
| 5,002,533 | 3/1991 | Jullien | 604/110 |
| 5,009,642 | 4/1991 | Sahi | 604/158 |
| 5,009,663 | 4/1991 | Broome | 606/232 |
| 5,026,353 | 6/1991 | Bartman | 604/192 |
| 5,030,210 | 7/1991 | Alchas | 604/247 |
| 5,034,005 | 7/1991 | Appling | 604/280 |
| 5,037,402 | 8/1991 | Bartman | 604/198 |
| 5,047,018 | 9/1991 | Gay et al. | 604/164 |
| 5,084,030 | 1/1992 | Byrne et al. | 604/198 |
| 5,085,648 | 2/1992 | Purdy et al. | 604/198 |
| 5,102,394 | 4/1992 | Lasaitis et al. | 604/164 |
| 5,102,401 | 4/1992 | Lambert | 604/264 |
| 5,104,382 | 4/1992 | Brinkerhoff et al. | 604/165 |
| 5,112,312 | 5/1992 | Luther | 604/177 |
| 5,116,353 | 5/1992 | Green | 606/184 |
| 5,120,317 | 6/1992 | Luther | 604/158 |
| 5,135,501 | 8/1992 | Cameron | 604/161 |
| 5,135,502 | 8/1992 | Koenig, Jr. et al. | 604/164 |
| 5,139,486 | 8/1992 | Moss | 604/164 |
| 5,147,332 | 9/1992 | Moorehead | 604/247 |
| 5,160,325 | 11/1992 | Nichols | 60/247 |
| 5,171,232 | 12/1992 | Castillo et al. | 604/280 |
| 5,195,962 | 3/1993 | Martin et al. | 604/43 |
| 5,205,817 | 4/1993 | Idemoto et al. | 604/22 |
| 5,205,829 | 4/1993 | Lituchy | 604/164 |
| 5,205,834 | 4/1993 | Moorehead et al. | 604/247 |
| 5,221,263 | 6/1993 | Sinko et al. | 604/161 |
| 5,224,938 | 7/1993 | Fenton, Jr. | 604/247 |
| 5,228,452 | 7/1993 | Samson | 128/772 |
| 5,242,410 | 9/1993 | Melker | 604/164 |
| 5,261,885 | 11/1993 | Lui | 604/247 |
| 5,263,957 | 11/1993 | Davison | 606/169 |
| 5,273,540 | 12/1993 | Luther et al. | 604/110 |
| 5,279,547 | 1/1994 | Costin | 604/22 |
| 5,279,551 | 1/1994 | James | 604/44 |
| 5,279,590 | 1/1994 | Sinko | 604/263 |
| 5,304,149 | 4/1994 | Morigi | 604/192 |
| 5,304,155 | 4/1994 | Lui | 604/247 |
| 5,312,345 | 5/1994 | Cole | 604/110 |
| 5,318,542 | 6/1994 | Hirsch et al. | 604/161 |
| 5,334,183 | 8/1994 | Wuchinich | 606/46 |
| 5,338,311 | 8/1994 | Mahurkar | 604/195 |
| 5,342,325 | 8/1994 | Lun et al. | 604/272 |
| 5,344,420 | 9/1994 | Hilal et al. | 606/28 |
| 5,357,961 | 10/1994 | Fields et al. | 128/658 |
| 5,359,996 | 11/1994 | Hood | 604/22 |
| 5,368,574 | 11/1994 | Antonacci et al. | 604/164 |
| 5,380,292 | 1/1995 | Wilson | 604/164 |
| 5,380,301 | 1/1995 | Prichard et al. | 604/281 |
| 5,401,257 | 3/1995 | Chevalier, Jr. et al. | 604/265 |
| 5,403,283 | 4/1995 | Luther | 604/164 |
| 5,419,766 | 5/1995 | Chang et al. | 604/110 |
| 5,423,764 | 6/1995 | Fry | 604/187 |
| 5,425,717 | 6/1995 | Mohiuddin | 604/160 |
| 5,425,718 | 6/1995 | Tay et al. | 604/165 |
| 5,441,497 | 8/1995 | Narciso, Jr. | 606/15 |
| 5,445,619 | 8/1995 | Burns | 604/192 |
| 5,472,430 | 12/1995 | Valliancourt et al. | 604/198 |
| 5,472,447 | 12/1995 | Abrams et al. | 606/169 |
| 5,486,159 | 1/1996 | Mahurkar | 604/4 |
| 5,489,269 | 2/1996 | Aldrich et al. | 604/280 X |
| 5,522,807 | 6/1996 | Luther | 604/264 |
| 5,531,701 | 7/1996 | Luther | 604/165 |
| 5,533,988 | 7/1996 | Dickerson et al. | 604/282 |
| 5,573,521 | 11/1996 | McFarlane | 604/282 |

FOREIGN PATENT DOCUMENTS

| | | |
|---|---|---|
| 2210270 | 1/1987 | United Kingdom . |
| 0247590 | 12/1987 | United Kingdom . |
| 2202747 | 1/1988 | United Kingdom . |
| 2202748 | 2/1988 | United Kingdom . |
| 2178322 | 7/1989 | United Kingdom . |
| 2231802 | 11/1989 | United Kingdom . |
| 2239604 | 12/1989 | United Kingdom . |
| 0216460 | 9/1990 | United Kingdom . |
| 2239607 | 7/1991 | United Kingdom . |
| 2240273 | 7/1991 | United Kingdom . |
| 2240477 | 8/1991 | United Kingdom . |
| 2240718 | 8/1991 | United Kingdom . |
| 2215612 | 12/1991 | United Kingdom . |
| 0576302 | 12/1993 | United Kingdom . |
| 0578367 | 1/1994 | United Kingdom . |
| 03035 | 5/1988 | WIPO . |
| 00178 | 1/1994 | WIPO . |

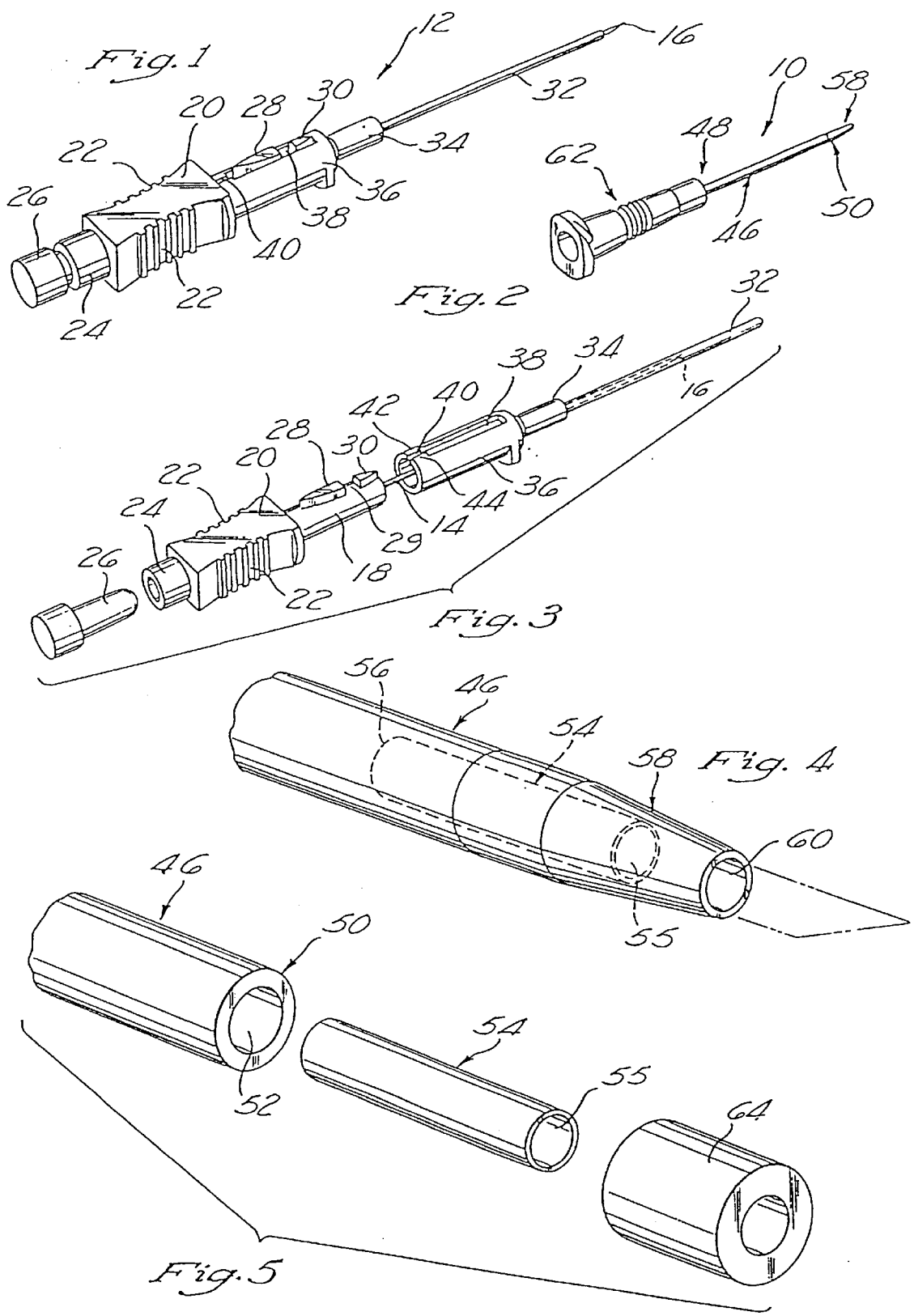

HARD TIP OVER-THE-NEEDLE CATHETER AND METHOD OF MANUFACTURING THE SAME

FIELD OF THE INVENTION

The present invention relates generally to medical devices, and more particularly to an improved over-the-needle catheter for use in the performance of therapeutic and diagnostic medical procedures. The catheter has a soft catheter body and a hard distal tip, and includes an abutment shoulder formed in close proximity to the distal tip which is adapted to abut a distal portion of an introducer. Such abutment prevents the tip from being pushed proximally over the introducer and collapsing the catheter body during the insertion of the catheter into an anatomical passage.

BACKGROUND OF THE INVENTION

Vascular/venous access devices for introducing catheters into a patient's vascular system are well known in the prior art. One of the most common of such devices comprises a through-the-needle catheter which is inserted into an anatomical passage through the use of cannula. The cannula itself typically comprises an elongate, metal needle which is inserted into the anatomical passage, with the catheter subsequently being advanced therethrough into the passage.

A common problem associated with the use of such prior art through-the-needle catheter systems arises during the removal of the cannula from the anatomical passage subsequent to the introduction of the catheter thereinto. Since, as previously indicated, the cannula typically comprises a rigid metal needle, it is desirable to immediately remove the cannula from within the anatomical passage subsequent to the advancement of the catheter thereinto to minimize trauma to the passage caused by the cannula's rigid structure and sharp piercing tip. However, once the catheter has been inserted into the anatomical passage, the cannula can typically only be removed from therewithin by retracting the same upwardly along the catheter, thereby undesirably exposing both the patient and the attendant medical personnel to accidental contact with the cannula, and more particularly the piercing tip of the needle.

In recognition of the problems and risks associated with the use of through-the-needle catheter systems, there is also known in the prior art over-the-needle catheter systems which have become widely utilized for venous/vascular access applications. In prior art over-the-needle catheter systems, a thin catheter having a hub attached to its proximal end is advanced over a rigid cannula, such as a needle, with the cannula and catheter being simultaneously inserted into a desired anatomical passage of a patient. Once the cannula and accompanying catheter have been introduced into the passage, the cannula is typically withdrawn from within the catheter interior, thus leaving the catheter operatively disposed within the passage. Thereafter, the hub mounted to the proximal end of the catheter may be used to fluidly connect the same to an infusion line or device.

A significant problem commonly associated with prior art over-the-needle catheter systems is that such catheters tend to travel axially (i.e., proximally) away from the distal piercing tip of the needle during the insertion process, thus collapsing the catheter. In this respect, the skin and tissue of the patient tend to resist the introduction of the distal end or tip of the catheter therethrough, thus pushing the distal end proximally away from the distal piercing tip of the introducer needle. Such proximal movement wrinkles the catheter in a bellows-like manner along the needle as the same is urged through the skin and tissue, with the distal end of the catheter traveling proximally away from the distal piercing tip of the needle.

Thus, such contemporary, prior art over-the-needle catheters must possess sufficient rigidity to prevent the same from traveling proximally relative to the cannula or needle upon which they are operatively positioned during the process of insertion into the anatomical passage. Because of the need for such rigidity, prior art over-the-needle catheters are typically incapable of being inserted through a substantial length of an anatomical passage (e.g., a vein or artery) without creating a relatively high risk of trauma and/or puncture.

In view of the foregoing, prior art over-the-needle catheters, though proving generally suitable for their intended purposes, have been found to possess deficiencies which detract from there overall effectiveness and reliability. As such, there exists a need in the prior art for an improved over-the-needle catheter which is not susceptible to collapsing or compressing during the process of insertion into an anatomical passage, yet is not so rigid so as to potentially cause trauma to the passage into which it is advanced.

SUMMARY OF THE INVENTION

In accordance with the present invention, there is provided a catheter for insertion into an anatomical passage through the use of an introducer. The catheter comprises an elongate, flexible catheter body which defines proximal and distal ends and a lumen extending longitudinally therethrough. Partially inserted into the distal end of the catheter body and protruding therefrom is a rigid, tubular sleeve which defines an abutment shoulder within the lumen of the catheter body. Disposed on and encapsulating the exposed portion of the sleeve is a distal tip member which defines a central opening. The central opening of the tip member communicates with the lumen via the sleeve. The abutment shoulder defined by the sleeve within the lumen is adapted to abut a portion of the introducer in a manner which inhibits the proximal movement of the tip member relative to the introducer. Such inhibition of movement prevents the tip member from being pushed proximally over the introducer and collapsing the catheter body during the insertion of the catheter into the anatomical passage.

In the preferred embodiment, the catheter body is formed of a first material having a first hardness, with the tip member being formed of a second material having a second hardness which exceeds the hardness of the first material. In particular, the first material has a Shore hardness A in the range of 60 to 90, and is preferably a soft polyurethane or silicone. The second material has a Shore hardness D of approximately 75, and is preferably polyurethane. The tubular sleeve is itself preferably fabricated from a radiopaque material, and in particular metal. The tip member of the catheter has a generally frusto-conical configuration, with the lumen of the catheter body and the central opening of the tip member each having generally circular cross-sectional configurations. In this respect, the diameter of the catheter body lumen preferably exceeds the diameter of the central opening of the tip member.

Further in accordance with the present invention, there is provided a method for manufacturing a catheter for insertion into an anatomical passage through the use of an introducer. The method comprises the initial step of partially inserting a tubular sleeve into the lumen of a catheter body such that the sleeve protrudes from one end of the catheter body and defines an abutment shoulder within the lumen. Thereafter, an annular member is advanced over the exposed portion of the sleeve and abutted against the distal end of the catheter body. The annular member is then inserted into a mold, with heat being applied thereto in an amount sufficient to facilitate the compression molding of the annular member into a frusto-conical tip member which encapsulates and captures the exposed portion of the sleeve. In particular, the annular member is inserted into a mold having a generally frusto-conical mold cavity, with a heating process being conducted to mold the annular member. Additionally, a mandrel is preferably inserted into the sleeve prior to heating the annular member so as to facilitate the formation of the central opening within the resultant tip member.

Further in accordance with the present invention, there is provided a catheter/introducer assembly comprising an introducer which includes a needle having a distal piercing tip and an abutment surface formed proximate to the piercing tip of the needle. The assembly further comprises a catheter which includes an elongate, flexible catheter body defining a distal end and a lumen extending longitudinally therethrough. Partially inserted into and protruding from the distal end of the catheter body is a rigid, tubular sleeve which defines an abutment shoulder within the lumen of the catheter body. Disposed on and encapsulating the exposed portion of the sleeve is a distal tip member defining a central opening which communicates with the lumen via the sleeve. The abutment shoulder is adapted to abut the abutment surface of the introducer in a manner which inhibits the proximal movement of the tip member relative to the introducer. Such abutment prevents the tip member from being pushed proximally over the introducer and collapsing the catheter body during the insertion of the catheter into an anatomical passage.

The present invention further comprises a method for inserting a catheter into an anatomical passage comprising the initial step of providing a catheter installed upon an introducer, wherein the catheter includes a distal tip member and a rigid, tubular sleeve which defines an abutment shoulder disposed proximate to the tip member. The abutment shoulder is adapted to abut a portion of the introducer in a manner which prevents the catheter from being pushed proximally over the introducer and collapsed during the insertion thereof into the anatomical passage. The method further comprises the steps of inserting the catheter and introducer into the anatomical passage, and removing the introducer from the catheter while maintaining the catheter within the anatomical passage.

BRIEF DESCRIPTION OF THE DRAWINGS

These, as well as other features of the present invention, will become more apparent upon reference to the drawings wherein:

FIG. 1 is a perspective view of an exemplary introducer for facilitating the insertion of the catheter of the present invention into an anatomical passage;

FIG. 2 is an enlarged perspective view of the catheter of the present invention;

FIG. 3 is an exploded perspective view of the introducer shown in FIG. 1;

FIG. 4 is a partial perspective view of the distal region of the catheter of the present invention;

FIG. 5 is an exploded view of the components used for the manufacture of the catheter of the present invention;

DETAILED DESCRIPTION OF THE PREFERRED EMBODIMENT

Figure 6:
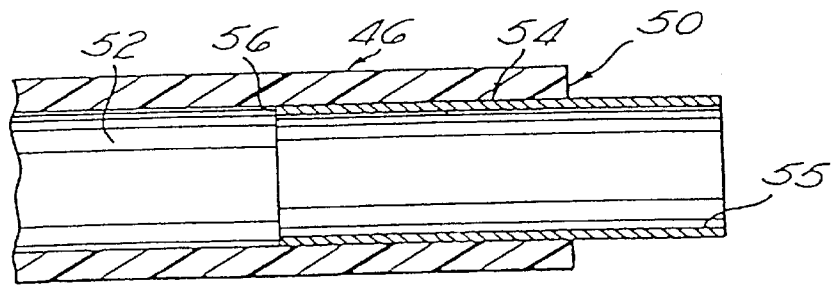
FIGS. 6–8 are partial cross-sectional views illustrating the sequence of steps used in the manufacture of the catheter of the present invention.

Referring now to the drawings wherein the showings are for purposes of illustrating a preferred embodiment of the present invention only and not for purposes of limiting the same, FIG. 2 perspectively illustrates the improved over-the-needle catheter 10 constructed in accordance with the present invention. FIGS. 1 and 3 perspectively illustrate an introducer 12 which may be utilized to facilitate the insertion or advancement of the catheter 10 into an anatomical passage such as a vein or artery.

Referring now to FIGS. 1 and 3, the introducer 12 for use with the catheter 10 is depicted without the catheter 10 being operatively positioned thereon. The introducer 12 comprises an elongate, tubular metal needle 14 which defines a sharp, distal piercing tip 16. The proximal end of the needle 14 is fluidly connected to a hollow, cylindrically configured base 18 which is integrally connected to and extends from a hollow handle 20 having finger holds 22 formed in opposed sides thereof. Extending from the end of the handle 20 opposite the base 18 is an annular boss 24 which communicates with the interior of the handle 20 and base 18. Removably inserted into the boss 24 is a porous, hydrophobic plug 26 which facilitates the venting of air from within the handle 20 and base 18, while preventing the undesirable leakage of blood therefrom.

Formed on the outer surface of the base 18 is a first wedge 28 and a second wedge 30. The first and second wedges 28, 30 are linearly aligned upon the base 18 in spaced relation to each other, with the first wedge 28 being larger (i.e., longer) than the second wedge 30. Defined between the first and second wedges 28, 30 is a gap or opening 29. The first and second wedges 28, 30 are oriented in a manner wherein the first wedge 28 is pointed toward the handle 20, with the second wedge 30 being pointed toward the needle 14. The use of the first and second wedges 28, 30 and intermediate opening 29 will be discussed in more detail below.

The introducer 12 further comprises a protective guard or sheath 32 which is slidably advanceable over the needle 14. The proximal end of the sheath 32 is attached to a cylindrically configured, tubular fitting, and preferably an engagement member 34 which is integrally connected to and extends axially from a tubular sleeve 36. Disposed within the sleeve 36 is a longitudinally extending slot 38. Extending longitudinally between the proximal end of the slot 38 and the open proximal end of the sleeve 36 opposite the end including the engagement member 34 formed thereon is a slit 40 which facilitates the formation of first and second tabs 42, 44 on either side thereof.

The introducer 12 of the present invention is assembled by proximally advancing the sleeve 36 and sheath 32 along the needle 14. The sleeve 36 is oriented such that the pointed end of the second wedge 30 is directed into the proximal end of the slit 40. As will be recognized, the continued proximal advancement of the sleeve 36 along the base 18 subsequent to the insertion of the pointed end of the second wedge 30 into the slit 40 facilitates the outward flexion of the first and second tabs 42, 44, thus allowing both the second wedge 30 and first wedge 20 to slide therethrough into the slot 38 which is sized to accommodate the first and second wedges 28, 30. When the first wedge 28 is received into the slot 38, the sleeve 36, and more particularly the first and second tabs 42, 44 thereof, resiliently return to their original positions, with the slit 40 extending longitudinally between the pointed end of the first wedge 28 and handle 20. As seen in FIG. 1, when the sleeve 36 assumes this position, a substantial portion of the length of the needle 14 is covered by the sheath 32, with only the piercing tip 16 protruding from the open distal end thereof. As will be recognized, the piercing tip 16 of the needle 14 remains exposed so as to allow for the use of the introducer 12.

Subsequent to the use of the introducer 12, the sleeve 36 and sheath 32 are advanced distally along the needle 14. As the sleeve 36 is urged distally, the pointed end of the first wedge 28 is extended into the distal end of the slit 40, thus again facilitating the outward flexion of the first and second tabs 42, 44 and allowing the first wedge 28 to be removed from within the slot 38. The distal advancement of the sleeve 36 along the base 18 is continued until the first and second tabs 42, 44 reach the opening 29 defined between the first and second wedges 28, 30. In this respect, upon reaching the opening 29, the first and second tabs 42, 44 resiliently return to their original positions, with the slit 40 extending longitudinally between the first and second wedges 28, 30. The extension of the first and second tabs 42, 44 into the opening 29 effectively locks the sleeve 36 in a position whereat the piercing tip 16 of the needle 14 is covered by the sheath 32 so as to prevent inadvertent needle sticks therewith.

As is apparent from the foregoing discussion regarding its structural characteristics, the introducer 12 with which the catheter 10 is preferably utilized is a non-stick or safety introducer due to its inclusion of the protective sheath 32 which covers the piercing tip 16 of the needle 14 subsequent to the use of the introducer 12. Thus, the introducer 12 prevents the inadvertent and potentially dangerous sticking of medical personnel with the needle 14, which is particularly important in view of the highly contagious and/or fatal nature of such diseases as AIDS and Hepatitis A. As previously explained, a substantial portion of the length of the needle 14 is initially covered by the sheath 32, with the piercing tip 16 remaining exposed to facilitate the introduction of the needle 14 (and hence the catheter 10) through the skin and tissue of a patient and into an anatomical passage such as a blood vessel. However, immediately upon the withdrawal of the needle 14 from within the anatomical passage, the sheath 32 is distally advanced over and covers the piercing tip 16 thereof to prevent inadvertent needle sticks.

It will be recognized that the introducer 12 as previously described is exemplary of an introducer which may be utilized with the catheter 10 of the present invention, and it not intended to serve as any limitation in relation to the present application. Those skilled in the art will recognize that the over-the-needle catheter 10 of the present invention as will hereinafter be described may likewise be utilized with a variety of different types of introducers. Indeed, the catheter 10 may optionally be utilized with simple needles and/or stylets. However, the greatest benefits are attained when the catheter 10 is utilized with an introducer, needle, or stylet having an abutment surface formed thereon which engages the catheter 10 so as to prevent the collapse thereof during the insertion process.

Referring now to FIGS. 2, 4, 5 and 9, the catheter 10 of the present invention which is insertable into an anatomical passage through the use of the previously described introducer 12 comprises an elongate, flexible catheter body 46 defining a proximal end 48, a distal end 50, and a lumen 52 extending longitudinally therethrough. The catheter body 46 is preferably formed of a soft first material having a Shore hardness A in the range of 60 to 90. In particular, the first material is preferably soft polyurethane or silicone, though other soft, biocompatible materials of similar hardness may be utilized as an alternative. Partially inserted into and protruding from the distal end 50 of the catheter body 46 is a rigid, tubular sleeve 54 which is preferably fabricated from a radiopaque material, and in particular metal. As seen in FIGS. 6–9, the sleeve 54 is advanced into the distal end 50 to a depth wherein approximately two-thirds of the length of the sleeve 54 is disposed within the lumen 52. Importantly, the proximal end of the sleeve 54 defines an abutment shoulder 56 within the lumen 52 of the catheter body 46 which extends about the inner, luminal surface thereof.

Disposed on and encapsulating the exposed portion of the sleeve 54 which protrudes from the distal end 50 is a distal tip member 58. In this respect, the tip member 58 covers the outer surface of the exposed portion of the sleeve 54, as well as the annular distal end thereof. The tip member 58 has a generally frusto-conical configuration and defines a central opening 60 which communicates with the lumen 52 via the bore of the sleeve 54. In the catheter 10, the lumen 52, central opening 60 and bore of the sleeve 54 each have generally circular cross-sectional configurations and are coaxially aligned with each other. Additionally, the diameter of the lumen 52 exceeds the diameter of the central opening 60 which is substantially equal to the diameter of the bore of the sleeve 54 (i.e., the diameter of the inner surface 55 thereof).

When disposed upon the exposed portion of the sleeve 54, the proximal end of the tip member 58 is abutted against the distal end 50 of the catheter body 46, with the distal end of the tip member 58 extending beyond the distal end of the sleeve 54. The tip member 58 is preferably formed of a second material which is harder than the first material of the catheter body 46, and has a Shore hardness D of approximately 75 or greater. The second material is preferably polyurethane, though other biocompatible materials of similar hardness may be used as an alternative.

Figure 9:
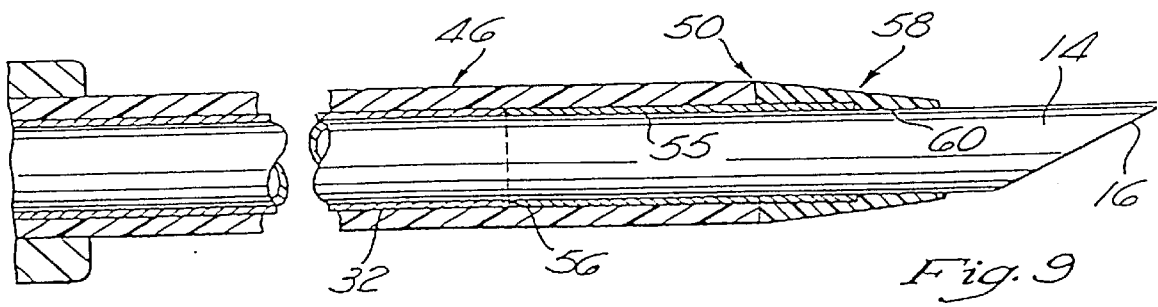
FIG. 9 is a cross-sectional view of the catheter of the present invention as operatively positioned upon the introducer.
Figure 10:
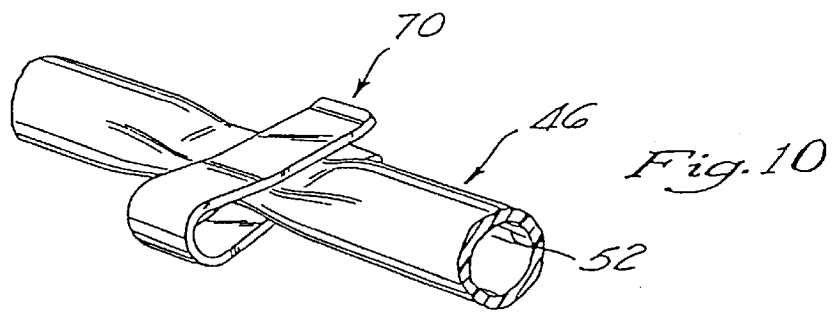
FIG. 10 is a partial perspective view illustrating the engagement of a hemostasis valve to the catheter of the present invention.

Referring now to FIGS. 1, 2 and 9, when configured for use with the introducer 12, the catheter 10 preferably includes a tubular female Luer lock 62 which is attached to the proximal end 48 of the catheter body 46. The catheter 10 (including the female Luer lock 62) is proximally advanced along the sheath 32 covering the needle 14, with the female Luer lock 62 being attached to the engagement member 34. Importantly, the catheter 10 is sized such that when attached to the introducer 12, only the piercing tip 16 of the needle 14 protrudes from the distal end of the tip member 58. In this respect, the sheath 32 (which covers a substantial portion of the length of the needle 14) is disposed within the lumen 52 of the catheter body 46.

Referring now to FIG. 9, as previously indicated, the sheath 32 is disposed within the lumen 52 of the catheter body 46 when the catheter 10 is properly interfaced to the introducer 12. Importantly, the catheter 10 is sized such that the distal end of the sheath 32 defines an abutment surface which directly abuts the abutment shoulder 56 defined by the sleeve 54. When the sheath 32 is abutted against the shoulder 56, the inner surface of the sheath 32, the inner surface 55 of the sleeve 54, and the central opening 60 of the tip member 58 are substantially flush with each other, and define a continuous passage having a diameter which slightly exceeds the diameter of the needle 14, thus allowing the same to be slidably extended therethrough.

Importantly, the abutment of the distal end of the sheath 32 against the abutment shoulder 56 of the sleeve 54 inhibits proximal movement of the tip member 58 relative to the sheath 32 and needle 14. As such, when the exposed piercing tip 16 of the needle 14 is inserted into an anatomical passage, the tip member 58 adjacent thereto is prevented from being pushed proximally over the sheath 32 and collapsing the catheter body 46, despite the interference of the tip member 58 against the skin and tissue of the patient. Thus, the catheter body 46 is maintained in its original, uncollapsed configuration during the insertion thereof into the anatomical passage since the tip member 58 is maintained in its position proximate to the piercing tip 16 of the needle 14 during the insertion process.

Figure 7:
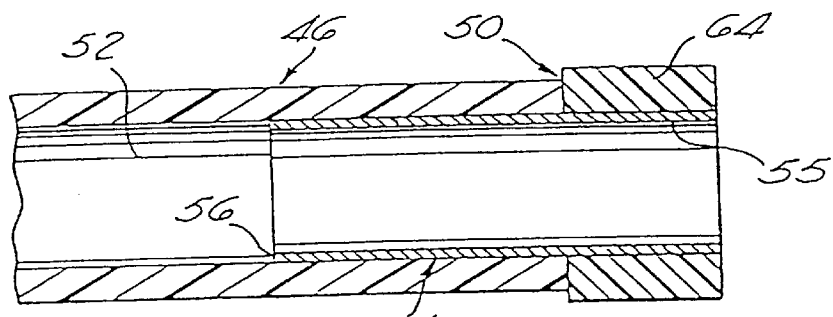

Having thus described the structure of the catheter 10, the preferred method of manufacturing the same will be discussed below. Referring now to FIGS. 5–8, the catheter 10 is preferably fabricated by initially inserting the sleeve 54 into the distal end 50 of the catheter body 46. As previously indicated, the sleeve 54 is advanced into the distal end 50 such that approximately two-thirds of the length thereof resides within the lumen 52. As seen in FIG. 7, subsequent to the insertion of the sleeve 54 into the catheter body 46, an annular member 64 which is preferably fabricated from a hard plastic material is advanced over the exposed portion of the sleeve 54 protruding from the distal end 50. The annular member 64 is abutted against the distal end 50 of the catheter body 46, and is sized such that the opposite end thereof is disposed slightly proximally relative to the distal end of the sleeve 54.

Figure 8:
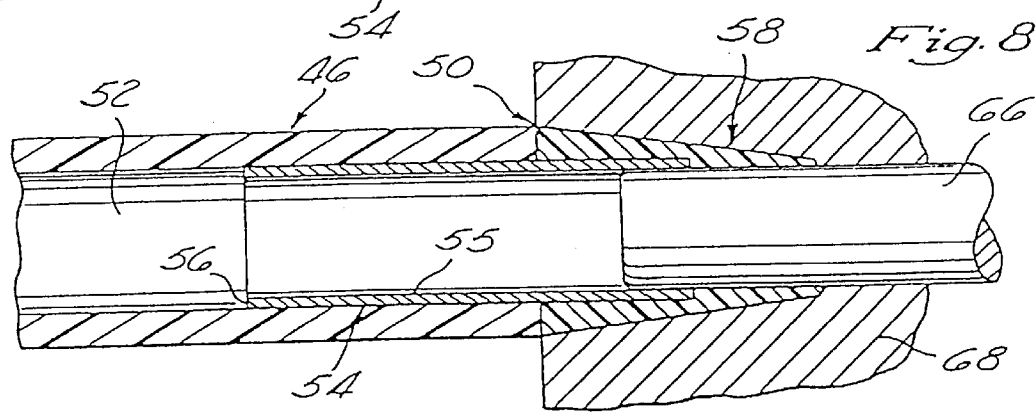

Referring now to FIG. 8, after the annular member 64 has been positioned upon the exposed portion of the sleeve 54, a cylindrically configured mandrel 66 is partially inserted into the distal end of the sleeve 54. Thereafter, the annular member 64 and mandrel 66 are inserted into a frusto-conically shaped cavity of a mold 68, with the annular member 64 being subjected to a heating process such as an RF heating process. Importantly, the heating of the annular member 64 facilitates the deformation thereof which causes the same to assume the shape of the frusto-conical mold cavity and encapsulate the exposed portion of the sleeve 54, including the distal end thereof. As will be recognized, once assuming the shape of the mold cavity and cooling/hardening, the annular member 64 forms the tip member 58.

Importantly, when heated the annular member 64 is prevented from flowing into the interior of the sleeve 54 by the mandrel 66 inserted thereinto. Additionally, the flow of the heated annular member 64 directly against the outer surface of the mandrel 66 facilitates the encapsulation of the distal end of the sleeve 54 thereby, as well as the formation of the central opening 60. Subsequent to the formation of the tip member 58, the same is removed from within the mold 68, with the mandrel 66 subsequently being removed from within the resultant catheter 10.

As previously explained, in the catheter 10 the catheter body 46 is fabricated from a soft, flexible material, with the tip member 58 being fabricated from a hard plastic material. Advantageously, the inclusion of the hard plastic tip member 58 avoids any "peel back" of the catheter 10 relative to the introducer 12 during the insertion process by increasing the structural integrity of the distal end thereof. The formation of the catheter body 46 from the soft, flexible material allows the catheter 10 to be advanced through tortuous anatomical passages with a minimal amount of difficulty. Due to the softness of the catheter body 46, the catheter 10 may be used in combination with a hemostasis valve 70 which may be selectively attached to the catheter body 46 as the introducer 12 is being removed from therewithin for preventing blood back-flow from the female Luer lock 62 of the catheter 10. The hemostasis valve 70 collapses the lumen 52 of the catheter body 46, thus preventing any fluid flow therethrough.

The improved over-the-needle catheter 10 of the present invention is utilized by initially advancing the same over the sheath 32 and needle 14 of the introducer 12 in the aforementioned manner. The exposed piercing tip 16 of the needle 14 is then urged into a desired anatomical passage, with the tip member 58 of the catheter 10 moving therewith. As previously indicated, the catheter body 46 is prevented from collapsing due to the contact between the sheath 32 and abutment shoulder 56 maintaining the tip member 58 proximate to the piercing tip 16. When the tip member 58 of the catheter 10 is positioned within the anatomical passage, the female Luer lock 62 is held firmly in place as the introducer 12 is withdrawn from within the catheter 10.

Prior to completely withdrawing the introducer 12 from within the catheter 10, the sheath 32 is deployed in the aforementioned manner so as to cover the piercing tip 16 of the needle 14, thereby preventing accidental needle sticks. In particular, deployment of the needle sheath 32 is preferably accomplished by continuing to withdrawal the introducer 12 from within the catheter 10 by retracting the handle 20, while maintaining the sleeve 36 stationary such that the slit 42 rides up and over the first wedge 28 and the first and second tabs 42, 44 become captured within the opening 29, thus locking the sheath 32 in its deployed position. This procedure assures that the sheath 32 is properly deployed prior to the piercing tip 16 of the needle 14 exiting the catheter 10.

Additional modifications and improvements of the present invention may also be apparent to those skilled in the art. For example, the length of the catheter body 46 may be increased substantially to facilitate its use in applications requiring that the tip member 58 of the catheter 10 be manipulated through an extended length of the vascular system. Thus, the particular combination of parts and steps described and illustrated herein is intended to represent only one embodiment of the present invention and is not intended to serve as limitations of alternative devices within the spirit and scope of the invention.

What is claimed is:

1. A catheter for insertion into an anatomical passage through the use of an introducer, said catheter comprising:

an elongate, flexible catheter body formed of a first material and defining proximal and distal ends and a lumen extending longitudinally therethrough;

a rigid, tubular sleeve partially inserted into the distal end of the catheter body and protruding therefrom, said sleeve being fixed to the catheter body and defining an abutment shoulder within the lumen thereof; and a distal tip member disposed on and encapsulating an exposed portion of the sleeve, said tip member being formed of a second material different from said first material and defining a central opening which communicates with the lumen via the sleeve;

said abutment shoulder being adapted to abut a portion of the introducer in a manner which inhibits proximal movement of the tip member relative to the introducer to prevent the tip member from being pushed proximally over the introducer and collapsing the catheter body during the insertion of the catheter into the anatomical passage.

2. The catheter of claim 1 wherein said first material is of a first hardness and said second material is of a second hardness which exceeds the first hardness of the first material.

3. The catheter of claim 2 wherein said first material has a Shore hardness A in the range of 60 to 90.

4. The catheter of claim 3 wherein the first material is silicone.

5. The catheter of claim 3 wherein the first material is soft polyurethane.

6. The catheter of claim 2 wherein said second material has a Shore hardness D of at least 75.

7. The catheter of claim 6 wherein the second material is polyurethane.

8. The catheter of claim 6 wherein the second material is a hard plastic.

9. The catheter of claim 1 wherein said sleeve is fabricated from metal.

10. The catheter of claim 1 wherein said sleeve is fabricated from a radiopaque material.

11. The catheter of claim 1 wherein said tip member has a generally frusto-conical configuration.

12. The catheter of claim 1 wherein the lumen and the central opening have generally circular cross-sectional configurations, with the diameter of the lumen exceeding the diameter of the central opening.

13. A catheter/introducer assembly for inserting a catheter into an anatomical passage, comprising:
   (a) an introducer comprising:
      (i) a needle having a distal piercing tip; and
      (ii) an abutment surface formed proximate to the piercing tip of the needle;
   (b) a catheter comprising:
      (i) an elongate, flexible catheter body defining a distal end and a lumen extending longitudinally therethrough;
      (ii) a rigid, tubular sleeve partially inserted into the distal end of the catheter body and protruding therefrom, said sleeve being fixed to the catheter body and defining an abutment shoulder within the lumen thereof; and
      (iii) a distal tip member disposed on and encapsulating the exposed portion of the sleeve, said tip member defining a central opening which communicates with the lumen via the sleeve;
   (c) the abutment shoulder of the catheter being abutted against the abutment surface in a manner which inhibits proximal movement of the tip member relative to the introducer to prevent the tip member from being pushed proximally over the introducer and collapsing the catheter body during the insertion of the catheter into the anatomical passage.

* * * * *